United States Patent
Balavoine et al.

(10) Patent No.: US 11,345,658 B2
(45) Date of Patent: May 31, 2022

(54) COMPOUNDS AND COMPOSITIONS COMPRISING THE SAME FOR TREATING HYPERTENSION OR HEART FAILURE

(71) Applicants: QUANTUM GENOMICS, Paris (FR); INSTITUT NATIONAL DE LA SANTE ET DE LA RECHERCHE MEDICALE, Paris (FR); CENTRE NATIONAL DE LA RECHERCHE SCIENTIFIQUE, Paris (FR); COLLEGE DE FRANCE, Paris (FR)

(72) Inventors: Fabrice Balavoine, Paris (FR); Delphine Compere, Sceaux (FR); Mathilde Keck, Le Perreux sur Marne (FR); Yannick Marc, Saint-Maur-des-Fosses (FR); Catherine Llorens-Cortes, Bures sur Yvette (FR); Solène E. Boitard, Thiais (FR)

(73) Assignees: QUANTUM GENOMICS, Paris (FR); INSTITUT NATIONAL DE LA SANTÉ ET DE LA RECHERCHE MÉDICALE, Paris (FR); CENTRE NATIONAL DE LA RECHERCHE SCIENTIFIQUE, Paris (FR); COLLEGE DE FRANCE, Paris (FR)

( * ) Notice: Subject to any disclaimer, the term of this patent is extended or adjusted under 35 U.S.C. 154(b) by 0 days.

(21) Appl. No.: 17/437,862

(22) PCT Filed: Mar. 11, 2020

(86) PCT No.: PCT/EP2020/056483
§ 371 (c)(1),
(2) Date: Sep. 10, 2021

(87) PCT Pub. No.: WO2020/182870
PCT Pub. Date: Sep. 17, 2020

(65) Prior Publication Data
US 2022/0041548 A1    Feb. 10, 2022

(30) Foreign Application Priority Data

Mar. 11, 2019   (EP) .................................... 19305286

(51) Int. Cl.
*C07C 323/58*   (2006.01)
*A61P 9/12*   (2006.01)
(Continued)

(52) U.S. Cl.
CPC ............ *C07C 323/58* (2013.01); *A61K 31/10* (2013.01); *A61K 31/198* (2013.01); *A61P 9/12* (2018.01)

(58) Field of Classification Search
CPC ... C07C 321/00; C07C 323/00; C07C 323/58; A61K 31/10; A61K 31/19; A61P 9/12
See application file for complete search history.

(56) References Cited

U.S. PATENT DOCUMENTS

| 7,582,797 B2 | 9/2009 | Roques et al. |
| 2006/0205695 A1 | 9/2006 | Roques et al. |

FOREIGN PATENT DOCUMENTS

FR  2 858 617  2/2005

OTHER PUBLICATIONS

Chauvel, E. N. et al. "Differential Inhibition of Aminopeptidase A and Aminopeptidase N by New β-Amino Thiols" *Journal of Medicinal Chemistry*, 1994, pp. 2950-2957, vol. 37, No. 18.
(Continued)

*Primary Examiner* — Theodore R. Howell
(74) *Attorney, Agent, or Firm* — Saliwanchik, Lloyd & Eisenschenk (57) ABSTRACT

The present invention relates to compounds, to compositions comprising the same, to methods for preparing the compounds, and the use of these compounds in therapy. In particular, the present invention relates to a compound that (Continued)

is useful in the treatment and prevention of primary and secondary arterial hypertension, ictus, myocardial ischaemia, cardiac and renal insufficiency, myocardial infarction, peripheral vascular disease, diabetic proteinuria, Syndrome X and glaucoma.

18 Claims, 3 Drawing Sheets

(51) Int. Cl.
*A61K 31/10* (2006.01)
*A61K 31/198* (2006.01)

(56) References Cited

OTHER PUBLICATIONS

Marc, Y. et al. "The role of the brain renin-angiotensin system in hypertension: Implications for new treatment" *Progress in Neurobiology*, 2011, pp. 89-103, vol. 95, No. 22.
Written Opinion in International Application No. PCT/EP2020/056483, dated May 25, 2020, pp. 1-6.

COMPOUNDS AND COMPOSITIONS COMPRISING THE SAME FOR TREATING HYPERTENSION OR HEART FAILURE

CROSS-REFERENCE TO RELATED APPLICATION

This application is the U.S. national stage application of International Patent Application No. PCT/EP2020/056483, filed Mar. 11, 2020.

FIELD OF THE INVENTION

The present invention relates to a compound, to a composition comprising the same, to a method for preparing the compound, and the use of this compound in therapy. In particular, the present invention relates to compounds that are useful in the treatment and prevention of primary and secondary arterial hypertension, ictus, myocardial ischemia, cardiac and renal insufficiency, myocardial infarction, peripheral vascular disease, diabetic proteinuria, Syndrome X and glaucoma.

BACKGROUND OF THE INVENTION

Essential Hypertension (HTN) and Heart Failure (HF) are two of the major pathologies in cardio-vascular disease. HTN affects approximately 1 billion individuals worldwide. It is a leading risk factor for coronary heart disease, HF, stroke and renal insufficiency. Despite the availability of effective and safe drugs, HTN and its concomitant risk factors remain uncontrolled in many patients. HF remains the leading cause of hospitalization for patients over 65 years old in western countries. HF affects one to five persons in a thousand in industrialized countries, all ages considered, with a prevalence of three to twenty in a thousand. Despite the large number of drugs available HF has a poor prognosis as the one-year survival, all stages considered, is about 65%. HF remains one of the first causes of cardiovascular death, consequently, there is still an unmet medical need to develop new efficient and safe classes of drugs.

The systemic renin-angiotensin system (RAS) is known to play a central role in blood pressure (BP) regulation and sodium metabolism. Systemic drugs targeting the RAS such as angiotensin I converting enzyme (ACE) inhibitors and angiotensin-II receptor type 1 ($AT_1$) antagonists are clinically effective in lowering BP and in preventing cardiovascular and renal morbidity and mortality in patients. Furthermore, activity of the renin-angiotensin aldosterone system (RAAS) is increased in patients with HF, and its maladaptive mechanisms may lead to adverse effects such as cardiac remodeling and sympathetic activation. Current evidence-based guideline IA recommended medicines for HF with reduced ejection fraction are mainly RAAS-acting molecules such ACE inhibitors or $AT_1$ receptor blockers and beta-adrenergic receptor blocking agents.

A functional RAS controlling cardiovascular functions and body fluid homeostasis is also present in the brain. Several studies suggest that increased activity of the brain RAS results in an increase in sympathetic neuron activity and vasopressin release and that hyperactivity of the brain RAS plays a critical role in mediating high BP in various animal models of HTN as well as cardiac remodeling and dysfunction in animals models of HF (Marc Y, Llorens-Cortes, C Progress in Neurobiology 2011, 95, pp 89-103; Westcott K V et al, Can. J. Physiol. Pharmacol. 2009, 87, pp 979-988). Because recent evidences support that angiotensin III (Ang III) through its action on AT1 receptor may be the true peptide effector of the brain RAS for the central control of BP, the brain aminopeptidase A (APA) the enzyme generating Ang III from angiotensin II (Ang II) in the brain constitutes a promising therapeutic target for treatment of HTN and for the treatment of HF.

Aminopeptidase A (APA, EC 3.4.11.7) is a membrane-bound zinc metalloprotease, which has been characterized as the enzyme responsible for the conversion of AngII into AngIII in the brain (Zini S et al, Proc. Natl. Acad. Sci. USA 1996, 93, pp 11968-11973). Several APA inhibitors have been developed so far (Chauvel E N et al, J. Med. Chem. 1994, 37, pp 1339-1346; Chauvel E N et al, J. Med. Chem. 1994, 37, pp 2950-2957; David C et al, J. Med. Chem. 1999, 42, pp 5197-5211; Georgiadis D et al, Biochemistry 2000, 39, pp 1152-1155; Inguimbert N et al, J. Peptide Res. 2005, 65, pp 175-188). Among them, EC33 ((3S)-3-amino-4-thiol-butyl sulfonate) was reported as a specific and selective APA inhibitor. Central infusions of EC33 were found to inhibit brain APA activity, to block the pressor responses to intracerebro-ventricular (icv) infusion of Ang II, and to lower BP in several experimental models of hypertension (Fournid-Zaluski M C et al Proc. Natl. Acad. Sci. USA 2004, 101, pp 7775-7780).

It was further demonstrated that acute oral administrations in conscious hypertensive DOCA-salt rats and SHR rats of RB150 (also known as firibastat) (15 to 150 mg/kg), a brain penetrating prodrug of EC33, induce a dose-dependent decrease in BP (Bodineau L et al, Hypertension 2008, 51, pp 1318-1325; Marc Y et al, Hypertension 2012, 60, pp 411-418). Interestingly, RB150 was found to lower BP in DOCA-salt rats and SHRs first by decreasing vasopressin release, increasing aqueous diuresis and natriuresis, thereby decreasing blood volume and BP to control values, and secondly by lowering sympathetic tone, thereby reducing vascular resistances and consequently decreasing BP. It was also reported that chronic oral administrations of RB150, and the ACE inhibitor, enalapril, are similarly effective in inhibiting cardiac dysfunction observed in rats with HF post myocardial infarction (MI) (Boitard S et al, Journal of Molecular and Cellular Cardiology 2019, 127, pp 215-222). RB150 is able to enter the brain after oral administration, block brain APA activity, normalize BP in hypertensive rats, and prevent cardiac dysfunction following MI in rats suggesting that brain APA inhibitors represent a new class of centrally-acting agents for the treatment of HTN and HF.

The present inventors have now identified novel compounds which act in vivo as potent brain APA inhibitors and to that respect can be effective in reducing arterial hypertension and can have utility in treating arterial hypertension and the diseases to which it indirectly and directly contributes such as heart failure. Said compounds also present a satisfactory bioavailability and pharmacokinetics parameters, which makes them good candidates for oral or parenteral administration.

SUMMARY OF THE INVENTION

Accordingly, the invention provides a compound with the following formula (I):

and more specifically having the following formula (II):

Wherein:
AH represents —CO$_2$H, —SO$_3$H, —PO$_3$H$_2$;
m is 1, 2 or 3;
R$_1$ and R$_2$ represent independently H, a C$_{1-6}$ alkyl, C$_{2-6}$ alkenyl or C$_{2-6}$ alkynyl group, each alkyl, alkenyl or alkynyl group being optionally substituted by at least one of the following radicals chosen from aryl, heterocycle, cycloalkyl, O-aryl, O-arylalkyl or O-cycloalkyl group; said aryl, heterocycle, cycloalkyl, O-aryl, O-arylalkyl, O-cycloalkyl group being optionally substituted with one or more radicals chosen from a halogen atom, an alkyl group, an alkoxy group, a haloalkyl group, a haloalkoxy group, an acyl group, an O-cycloalkyl group, a heteroalkyl group, an O-aryl group, an O-arylalkyl group, an aryl group, a heterocycle group or an arylalkyl group; a pharmaceutical salt, solvate, zwitterionic form or any prodrug thereof.

In another aspect, the present invention discloses a composition comprising said compound of formula (I) and more specifically of formula (II). The composition is more particularly a pharmaceutical composition. The present invention provides therefore a pharmaceutical composition comprising at least one compound of the invention, preferably in association with a pharmaceutically acceptable diluent or carrier.

According to another aspect, the invention relates to a method for prevention or treatment of arterial hypertension and indirectly and directly related diseases, comprising administration of a therapeutically effective amount of a compound of this invention. In another aspect, the present invention provides a compound of the invention for use in therapy or medicine as an Active Pharmaceutical Ingredient, and in particular, in human medicine, and more specifically for the treatment of arterial hypertension and indirectly and directly related diseases or disorders.

In another aspect, the present invention provides the use of the compound of the invention for the manufacture of a medicament for the treatment of arterial hypertension and indirectly and directly related diseases or disorders.

In another aspect, the present invention provides a method of treatment of a patient suffering from arterial hypertension and indirectly and directly related diseases comprising the administration of a therapeutically effective amount of a compound of the invention.

DETAILED DESCRIPTION

The present invention thus relates to a compound with the following formula (I):

and more specifically having the following formula (II):

wherein:
AH represents —CO$_2$H, —SO$_3$H, —PO$_3$H$_2$;
m is 1, 2 or 3;
R$_1$ and R$_2$ represent independently H, a C$_{1-6}$ alkyl, C$_{2-6}$ alkenyl or C$_{2-6}$ alkynyl group, each alkyl, alkenyl or alkynyl group being optionally substituted by at least one of the following radicals chosen from aryl, heterocycle, cycloalkyl, O-aryl, O-arylalkyl or O-cycloalkyl group; said aryl, heterocycle, cycloalkyl, O-aryl, O-arylalkyl, O-cycloalkyl group being optionally substituted with one or more radicals chosen from a halogen atom, an alkyl group, an alkoxy group, a haloalkyl group, a haloalkoxy group, an acyl group, an O-cycloalkyl group, a heteroalkyl group, an O-aryl group, an O-arylalkyl group, an aryl group, a heterocycle group or an arylalkyl group.

The present invention provides compounds according to the invention for use or in methods of prevention or treatment of arterial hypertension and diseases to which arterial hypertension directly or indirectly contributes. Such diseases include diseases of the heart, the peripheral and cerebral vascular system, the brain, the eye and the kidney. In particular diseases include primary and secondary arterial hypertension, ictus, myocardial ischemia, cardiac or renal insufficiency, myocardial infarction, peripheral vascular disease, diabetic proteinuria, Syndrome X and glaucoma.

As used herein, "a compound of the invention" means a compound described above or a prodrug thereof or a pharmaceutically acceptable salt, solvate or any zwitterionic form thereof.

Within the context of the present invention:
The term "alkyl" or "Alk" means a monovalent or divalent, linear or branched, saturated hydrocarbon chain, comprising 1-6 carbon atoms, such as the methyl, ethyl, propyl, isopropyl, n-butyl, iso-butyl, sec-butyl, tert-butyl, tert-butyl-methyl, n-pentyl, or n-hexyl group. In a preferred embodiment, the "alkyl" is a methyl, an ethyl, a propyl, an isopropyl, or a tert-butyl, more preferably a methyl or ethyl group.

The term "alkenyl" refers to an unsaturated, linear or branched aliphatic group comprising at least one carbon-carbon double bound. The term "$(C_2\text{-}C_6)$alkenyl" more specifically includes ethenyl, propenyl, isopropenyl, butenyl, isobutenyl, pentenyl, or hexenyl group.

The term "alkynyl" refers to an unsaturated, linear or branched aliphatic group comprising at least one carbon-carbon triple bound. The term "$(C_2\text{-}C_6)$alkynyl" more specifically includes ethynyl, propynyl, butynyl, pentynyl, isopentynyl, or hexynyl group.

The term "acyl" means a —C(O)R group, where R is an alkyl group as defined earlier or a phenyl group. An acyl group includes for example acetyl, ethylcarbonyl, or benzoyl group.

The term "alkoxy" or "alkyloxy" means a -OAlk group wherein Alk is an alkyl group as defined above. An alkoxy group includes for example methoxy, ethoxy, n-propyloxy, or tert-butyloxy group.

The term "aryl" or "Ar" means an aromatic monocyclic or bicyclic system comprising 4-10 carbon atoms, it being understood that in the case of a bicyclic system, one of the cycles is aromatic and the other cycle is aromatic or unsaturated. Aryl groups include for example phenyl, naphthyl, indenyl, or benzocyclobutenyl groups, preferably a phenyl group.

The term "arylalkyl" means a -Alk-Ar group, wherein Alk represents an alkyl group as defined earlier, and Ar represents an aryl group as defined earlier.

The term "cycloalkyl" means a saturated monocyclic or polycyclic system, such as a fused or bridged bicyclic system, comprising 3-12 carbon atoms, such as the cyclopropyl, cyclobutyl, cyclopentyl, cyclohexyl, cycloheptyl, cyclooctyl, adamantly, decalinyl, or norbornyl groups.

The term "O-cycloalkyl" means a cycloalkyl group as defined earlier connected to the remainder of the molecule through an oxygen atom. O-cycloalkyl includes for example the O-cyclopentyl or O-cyclohexyl group.

The term "O-aryl" means an aryl group as defined earlier connected to the remainder of the molecule through an oxygen atom. O-aryl includes for example the O-phenyl group.

The term "O-arylalkyl" means an arylalkyl group as defined earlier connected to the remainder of the molecule through an oxygen atom. O-arylalkyl includes for example the O-benzyl group.

The term "haloalkyl" means a linear or branched saturated hydrocarbon chain, comprising 1-6 carbon atoms and substituted with one or more, and notably 1-6 halogen atoms, such as the trifluoromethyl or 2,2,2-trifluoroethyl groups.

The term "haloalkoxy" means a linear or branched saturated hydrocarbon chain, comprising 1-6 carbon atoms and substituted with one or more, and notably 1-6 halogen atoms, said chain being connected to the compound through an oxygen atom, such as the trifluoromethoxy or 2,2,2-trifluoroethoxy groups.

The term "heterocycle" means a saturated, unsaturated or aromatic, fused, spiro-fused or bridged, monocyclic or bicyclic system with 3-12 members, comprising 1-4 heteroatoms, either identical or different, selected from oxygen, sulfur and nitrogen, and possibly containing 1 or 2 oxo (=O) or thioxo (=S) groups, it being understood that in the case of a bicyclic system, one of the cycles may be aromatic and the other cycle is aromatic, saturated or unsaturated. Heterocycle includes for example piperidyl, piperazyl, furyl, thienyl, pyrrolyl, pyrazolyl, imidazolyl, pyridyl, pyrimidyl, pyrazinyl, pyradizinyl, benzofuryl, benzothienyl, indolyl, quinolyl, isoquinolyl, benzodioxolyl, benzodioxinyl, benzo[1,2,5]thiadiazolyl, benzo[1,2,5]oxadiazolyl, [1,2,3]triazolyl, or [1,2,4]triazolyl groups.

The term "heteroalkyl" means a linear or branched saturated hydrocarbon chain, comprising 1 to 5 carbon atoms and at least 1 or 2 heteroatoms, such as sulfur, nitrogen or oxygen atoms. Heteroalkyl for example includes —O(CH$_2$)$_2$OCH$_3$ or —(CH$_2$)$_2$OCH$_3$ group.

The term "halogen atom" means fluorine, bromine, chlorine or iodine atom.

The term "protective group" or "protection group" means the group which selectively blocks the reactive site in a multifunctional compound so that a chemical reaction may be selectively carried out at another non-protected reactive site, with the meaning conventionally associated with the latter in synthesis chemistry.

In the present invention, the term "pharmaceutically acceptable" refers to which can be used in the preparation of a pharmaceutical composition which is generally safe, non-toxic and not undesirable, biologically or otherwise, and which is commonly accepted for a veterinary or human pharmaceutical use.

The term "pharmaceutically acceptable salts" of the compounds of the invention include conventional salts formed from pharmaceutically acceptable inorganic or organic acids or bases as well as quaternary ammonium salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic etc. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts.

For example, preferred salt forms include chlorhydrate.

The term "pro-drug" means a chemical derivative of the compound, object of the invention, which generates in vivo said compound by one or more spontaneous chemical reactions with the physiological medium, notably by enzymatic reactions, photolysis and/or metabolic reactions. In the present case, pro-drugs of the compounds of the invention generate in vivo compounds identified as inhibitors of aminopeptidase A.

A pro-drug may be obtained by derivatizing functional group with specific labile moieties. The pro-drug with an acid function (such as phosphinic acid, carboxylic acid, sulfonic acid or phosphonic acid) notably comprises ester, the pro-drug with amine function notably comprises [(2-methylpropanoyl)oxy]ethoxycarbonyl.

Other examples are described in T. Higuchi and V. Stella, "Pro-drugs as Novel Delivery system", Vol. 14, A.C.S Symposium Series, American Chemical Society (1975) and "Bioreversible Carriers in Grug Design: Theroy and Application", edited by E. B. Roche, Pergamon Press: New York, 14-21 (1987).

According to the invention, the term "isomer" refers to compounds of the invention which have identical molecular formulae as identified herein but which differ by nature or in the binding sequence of their atoms or in the layout of their atoms in space. Isomers which differ in the layout of their atoms in space are designated by "stereoisomers". Stereoisomers which are not mirror images of each other, are designated as "diastereoisomers", and stereoisomers which are non-superposable mirror images of each other are designated as "enantiomers" or "optical isomers". "Stereoisomers" refer to racemates, enantiomers and diastereoisomers.

The person skilled in the art will recognize that stereocenters exist in the compounds of the invention. Any chiral center of a compound of the invention can be (R), (S) or racemate. Accordingly, the present invention includes all possible stereoisomers and geometric isomers of the compounds of formula (I) and includes not only racemic compounds but also the optically active isomers as well. According to a preferred embodiment, compounds of the invention is of formula (II). When a compound of formula (I) is desired as a single enantiomer, it may be obtained either by resolution of the final product or by stereospecific synthesis from either isomerically pure starting material or any suitable intermediate. Resolution of the final product, an intermediate or a starting material may be effected by any suitable method known in the art. See, for example, Stereochemistry of Carbon Compounds by E. L. Eliel (Mcgraw Hill, 1962) and Tables of Resolving Agents by S. H. Wilen.

The person skilled in the art will recognize that the compounds of the invention may contain at least one positive and one negative charge so that the compounds of the invention includes zwitterionic forms thereof. In chemistry, a zwitterion (also called an inner salt), is a molecule with two or more functional groups, of which at least one has a positive and one has a negative electrical charge and the charges on the different functional groups balance each other out, and the molecule as a whole is electrically neutral. The pH where this happens is known as the isoelectric point. Accordingly, any zwitterionic forms of the compounds of the invention including prodrugs thereof are within the scope of the present invention.

The specialist in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of formula (I) or (II) are within the scope of the present invention.

It will also be appreciated by the specialist in organic chemistry that many organic compounds can exist in more than one crystalline form. For example, crystalline form may vary from solvate to solvate. Thus, all crystalline forms of the compounds of the invention or the pharmaceutically acceptable solvates thereof are within the scope of the present invention.

References herein to a compound according to the invention include both compounds of formula (I) or (II) and their pharmaceutically acceptable salts, solvates, zwitterionic forms or prodrugs.

According to a particular embodiment, the compounds of the present invention correspond to general formula (I) and more specifically formula (II), wherein $R_1$ and $R_2$ represent independently H or a $C_{1-6}$ alkyl, each alkyl group being optionally substituted by at least one of the following radicals chosen from aryl, heterocycle or cycloalkyl group; said aryl, heterocycle, cycloalkyl group being optionally substituted with one or more radicals chosen from a halogen atom, an alkyl group, an alkoxy group, a haloalkyl group, a haloalkoxy group, an acyl group, an O-cycloalkyl group, a heteroalkyl group, an O-aryl group, an O-arylalkyl group, an aryl group, a heterocycle group or an arylalkyl group.

According to another particular embodiment, the compounds of the present invention correspond to general formula (I) and more specifically formula (II), wherein $R_1$ and $R_2$ are both H, or, alternatively, $R_1$ is H and $R_2$ is a benzyl (i.e. —$CH_2$-phenyl) or phenethyl group (i.e. —$(CH_2)_2$phenyl).

According to preferred embodiments, the compounds of the present invention correspond to general formula (I) and more specifically formula (II), wherein one, two, three or four of the following features are fulfilled, preferably each feature is fulfilled:
m is 2 or 3; and/or
AH is $CO_2H$ or $SO_3H$; and/or
$R_1$ is H; and/or
$R_2$ is H or an alkyl, preferably an alkyl substituted by a phenyl group.

According to more preferred embodiments, the compounds of the present invention correspond to general formula (I) and more specifically formula (II), wherein one, two or three of the following features are fulfilled, preferably each feature is fulfilled:
m is 2; and/or
AH is $SO_3H$; and/or
$R_1$ and $R_2$ are both H, or, alternatively, $R_1$ is H and $R_2$ is a phenethyl group (i.e. —$(CH_2)_2$phenyl).

According to specific embodiments, the compound of the invention is selected from the group consisting of:
(2R)-2-amino-3-{[(2S)-2-amino-4-sulfobutyl]disulfanyl}propanoic acid,
(2R)-2-amino-3-{[(3S,4S)-4-amino-1-phenyl-6-sulfohexan-3-yl]disulfanyl}propanoic acid and a pharmaceutical salt, solvate, zwitterionic form or any prodrug thereof.

According to a specific embodiment, the compounds of the invention are for use as medicine.

The compounds of the invention are conveniently administered in the form of pharmaceutical compositions. Such compositions may conveniently be presented for use in conventional manner in admixture with one or more physiologically acceptable carriers or excipients. The carrier(s) must be "acceptable" in the sense of being compatible with the other ingredients of the formulation and not deleterious to the subject receiving them.

While it is feasible that compounds of the present invention may be therapeutically administered as a raw chemical, it is also possible to present the active ingredient as a pharmaceutical formulation.

Accordingly, the present invention further provides a pharmaceutical composition comprising a compound of the present invention in association with one or more pharmaceutically acceptable carriers and, optionally, other active ingredients.

The pharmaceutical compositions include those suitable for oral, parenteral (including subcutaneous e.g. by injection or by depot tablet, intradermal, intrathecal, intraocular, intramuscular e.g. by depot and intravenous), ocular, rectal and topical (including dermal (i.e. on the skin), buccal and sublingual) or in a form suitable for administration by inhalation or insufflation, although the most suitable route may depend upon for example the condition and disorder of the recipient. The compositions may conveniently be presented in unit dosage form and may be prepared by any of the methods well known in the art of pharmacy. All methods include the step of associating the compounds of the invention, optionally with at least one other active ingredient, with the carrier which constitutes one or more accessory ingredients. In general the formulations are prepared by uniformly and intimately associating the active ingredient with liquid carriers or finely divided solid carriers or both and then, if necessary, shaping the product into the desired formulation.

Pharmaceutical compositions suitable for oral administration may be presented as discrete units such as capsules, cachets or tablets (e.g. chewable tablets in particular for pediatric administration) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a other conventional excipients such as binding agents (for example, syrup, gum arabic, gelatin, sorbitol, tragacanth, mucilage of starch, polyvinylpyrrolidone or hydroxymethyl cellulose), fillers (for example, lactose, sucrose, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycolate) or wetting agents, such as sodium lauryl sulfate. Molded tablets may be made by molding in a suitable machine a mixture of the powdered compound moistened with an inert liquid diluent. The tablets may optionally be coated or scored and may be formulated so as to provide slow or controlled release of the active ingredient therein. The tablets may be coated according to methods well-known in the art.

Alternatively, the compounds of the present invention may be incorporated into oral liquid preparations such as aqueous or oily suspensions, solutions, emulsions, and such as syrups or elixirs, for example. Moreover, pharmaceutical compositions (or formulations) containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or arabic gum; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. These preparations may also be formulated as suppositories, e.g., containing conventional suppository excipients such as cocoa butter or other glycerides.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of a sterile liquid carrier, for example, water-for-injection, immediately prior to use. Extemporaneous injection solutions and suspensions may be prepared from sterile powders, granules and tablets of the kind previously described.

Compositions for rectal administration may be presented as a suppository with the usual carriers such as cocoa butter, hard fat or polyethylene glycol.

Formulations for topical administration in the mouth, for example buccally or sublingually, include lozenges comprising the active ingredient in a flavored excipient such as sucrose and arabic gum or tragacanth, and pastilles comprising the active ingredient in an excipient such as gelatin and glycerin or sucrose and arabic gum. For topical administration onto the skin, the compounds may be formulated as creams, gels, ointments or lotions or as a transdermal patch. For ocular administration, the compositions can be a liquid solution (such as eye-drop solution), a gel, a cream or any type of ophthalmic compositions.

The compounds may also be formulated as depot preparations. These long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For intranasal administration the compounds of the present invention may be used, for example as a liquid spray, as a powder or in the form of drops.

For administration by inhalation the compounds according to the present invention are conveniently delivered in the form of an aerosol spray presentation from a pressurised container or a nebuliser, with the use of a suitable propellant, e.g. 1,1,1,2-trifluoroethane (HFA 134A) and 1,1,1,2,3,3,3,-heptafluoropropane (HFA 227), carbon dioxide or other suitable gas. In the case of a pressurised aerosol the exact dosage may be determined by providing a valve adapted to deliver a metered amount. Capsules and cartridges of e.g. gelatin for use in an inhaler or insufflator may be formulated so as to contain a powder mix of a compound of the present invention and a suitable powder excipient such as lactose or starch.

In addition to the ingredients particularly mentioned above, the formulations may include other agents conventional in the art having regard to the type of formulation in question, for example those suitable for oral administration may include flavoring agents.

It will be appreciated by the person skilled in the art that reference herein to treatment extends to prophylaxis as well as the treatment of established diseases or symptoms. Moreover, it will be appreciated that the amount of a compound of the present invention required for use in treatment will vary with the nature of the condition being treated and the age and the condition of the patient and will be ultimately at the discretion of the attendant physician or veterinarian.

The patient can be any mammal, including human or non-human mammal. The invention is more specifically addressed to human mammals, more specifically adults. In general, doses employed for adult human treatment will typically be in the range of 0.02-5000 mg per day, preferably 1-1500 mg per day. The desired dose may conveniently be presented in a single dose or as divided doses administered at appropriate intervals, for example as two, three, four or more sub-doses per day. The formulations according to the present invention may contain between 0.1-99% of the active ingredient, conveniently from 30-95% for tablets and capsules and 3-50% for liquid preparations.

The compounds of the present invention for use in the present invention may be used in association with one or more other therapeutic active agents, for example, beta-adrenergic receptor antagonists, calcium channel blocking agents, thiazide diuretics, angiotensin receptor antagonists and angiotensin converting enzyme inhibitors. The present invention thus provides in a further aspect the use of a combination comprising a compound of the invention with a further therapeutic agent in the treatment of arterial hypertension.

When the compounds of the present invention are used in association with other therapeutic agents, the compounds may be administered either sequentially or simultaneously by any suitable route.

The associations referred to above may suitably be presented for use in the form of a pharmaceutical formulation and thus pharmaceutical formulations comprising an association as defined above optimally together with a pharmaceutically acceptable carrier or excipient are a further aspect of the present invention. The individual components of such associations may be administered either sequentially or simultaneously in separate or combined pharmaceutical formulations.

When combined in the same formulation it will be appreciated that the two compounds must be stable and compatible with each other and the other components of the formulation and may be formulated for administration. When formulated separately they may be provided in any suitable formulation, suitably in a manner known for such compounds in the art.

When a compound of the present invention is used in association with a second therapeutic agent active against the same disease, the dose of each compound may differ from that administered when the compound is used alone. Appropriate doses will be readily determined by the person skilled in the art.

In another aspect, a subject of the present invention is a method for the prevention or treatment of arterial hypertension and of directly and indirectly related diseases, comprising the administration of a therapeutically effective amount of a compound of the present invention.

In another aspect, the present invention provides compounds of the present invention for use in therapeutics, and in particular in veterinary or human medicine.

The invention also relates to the use of a compound of formula (I) or (II), as a selective inhibitor with regard to aminopeptidase A.

In another aspect, the present invention provides the use of a compound of the present invention, for producing or preparing a medicinal product for use in the treatment of arterial hypertension and of directly and indirectly related diseases.

In another aspect, the present invention provides a method of treating a patient suffering from arterial hypertension and from directly and indirectly related diseases, comprising the administration to said patient of a therapeutically effective amount of a compound of the present invention.

The present invention provides methods for the prevention or treatment of arterial hypertension and of diseases to which arterial hypertension directly or indirectly contributes. These diseases comprise heart disease, heart failure, stroke, peripheral and/or cerebral vascular system diseases, brain, eye and kidney diseases. In particular, the diseases comprise primary and secondary arterial hypertension, an ictus, myocardial ischemia, cardiac insufficiency or renal insufficiency, myocardial infarction, a peripheral vascular disease, diabetic proteinuria, syndrome X, glaucoma, neurodegenerative diseases and memory disorders.

The compounds of formula (I), or preferably (II), can be prepared by several methods. The starting products are commercial products or products prepared according to known synthesis from commercial compounds or known to one skilled in the art. More specifically, the method for preparing the compounds of the invention is as described below, and comprises therefore the following successive steps.

The compounds of formula (I) can be prepared from intermediate (V) by the following process:

Wherein:

$R_1$, $R_2$, m and AH are as defined above,

X, Y and Z are protective groups of amino or acidic functions and,

A represents —$SO_3W$, —$CO_2W$ or —$P(O)(OW)_2$, with W being selected from the group consisting of an alkyl and arylalkyl group;

According to this synthesis route, intermediate (V) is hydrolysed in basic conditions with lithine reagent (LiOH.$H_2O$), for example in a mixture of methanol and water, leading to intermediate (IV). Intermediate (IV) can react with protected 2-amino-3-mercaptopropanoic acid of formula (VI) in order to provide compound of formula (III). Then, deprotection of compound (III) can occur by refluxing of trifluoroacetic acid in the presence of anisole to lead to the formation of the compound of the present invention of formula (I).

In the case where $R_1$=$R_2$=H, compound of formula (I) can be obtained from intermediate (V), whose synthesis is described in the patent WO2012/045849.

In the case where $R_1 \neq R_2 \neq H$, compound of formula (I) can be obtained from precursor of the following formulae (VII) leading to intermediate (V), Wherein X and A are defined above.

Synthesis of precursor (VII) is also described in patent WO2012/045849.

Alternatively, the compounds of formula (I) can be prepared from intermediate (VIII) by the following process:

According to this alternative synthetic route, homodimer of formula (VIII) can react with protected 2-amino-3-mercaptopropanoic acid of formula (VI) in order to provide compound of formula (III). Then, deprotection of compound (III) can occur by refluxing of trifluoroacetic acid in the presence of anisole to lead to the formation of the compound of the present invention of formula (I).

Intermediate (VIII) is also described in patent WO2012/045849.

The following Examples give further details of the invention, they should not be construed however as constituting a limitation thereto.

EXAMPLES

The starting products used are commercial products or products prepared according to known synthesis from commercial compounds or known to one skilled in the art. The exemplified preparation lead to synthesis intermediates useful for preparing the compounds of the invention.

The structures of the compounds described in the examples were determined according to the usual spectrophotometric techniques (nuclear magnetic resonance (NMR), mass spectrometry including electrospray ionisation (ESI) . . . ) and purity was determined by high performance liquid chromatography (HPLC).

Synthesis intermediates and compounds of the invention are named according to the IUPAC (The International Union of Pure and Applied Chemistry) nomenclature and described in their neutral form.

The following abbreviations have been used:

(Boc)$_2$O: di-tert-butyl dicarbonate
AcSK: potassium thioacetate
AcOH: acetic acid
Cbz: carboxybenzyl
CH$_2$Cl$_2$ or DCM: dichloromethane
CHCl$_3$: chloroform
cHex: cyclohexane
DMF: dimethylformamide
DIPEA: N,N-diidopropylethylamine
Et$_2$O: diethyl ether
EtOAc: ethyl acetate
EtOH: ethanol
HCl: hydrochloric acid
I$_2$: iodine
i-PrOH: isopropanol
K$_2$CO$_3$: potassium carbonate
LiAlH(OtBu)$_3$: lithium tri-tert-butoxyaluminum hydride
LiAlH$_4$: lithium aluminium hydride
LiOH.H$_2$O: lithium hydroxide monohydrate (lithine)
MeOH: methanol
MTBE: methyl tert-butyl ether
Na$_2$S$_2$O$_3$: sodium thiosulfate
Na$_2$SO$_4$: sodium sulfate
NaBH$_4$: sodium borohydride
NaHCO$_3$: sodium bicarbonate
NEt$_3$: tritethylamine
NH$_4$Cl: ammonium chloride
TBTU: 2-(1H-Benzotriazole-1-yl)-1,1,3,3-tetramethylaminium tetrafluoroborate
TFA: trifluoroacetic acid
THF: tetrahydrofurane
Eq.: equivalent
ESI: Electrospray Ionisation
HPLC: High Performance Liquid Chromatography
NMR: Nuclear Magnetic Resonance Preparation of tert-butyl (2R)-2-{[(tert-butoxy)carbonyl]amino}-3-sulfanylpropanoate Step 1: (2R)-2-{[(tert-butoxy)carbonyl]amino}-3-{[(2R)-2-{[(tert-butoxy)carbonyl]amino}-2-carboxyethyl]disulfanyl}propanoic acid Di-tert-butyl-dicarbonate (12.7 g, 58.2 mmol) was added to a cooled solution at 0° C. of L-cystine, also called (2R)-2-amino-3-{[(2R)-2-amino-2-carboxyethyl]disulfanyl}propanoic acid (5.0 g, 20.8 mmol) in a mixture of aqueous solution of sodium carbonate (10%, 72 mL) and dioxane (72 mL). The medium was allowed to warm to room temperature. After stirring overnight, the mixture was concentrated under vacuum. The residue was partitioned between EtOAc and water. The cooled mixture at 0° C. was carefully acidified to pH 1 with 2N HCl solution. The aqueous layer was extracted (EtOAc), combined organic layer was washed with brine, dried over Na$_2$SO$_4$, filtered and the filtrate was concentrated under reduced pressure to afford the title compound (10.1 g, quantitative yield) as a white solid.

MS (ESI$^-$): [M−H]$^-$=439.3

Step 2: tert-butyl (2R)-3-{[(2R)-3-(tert-butoxy)-2-{[(tert-butoxy)carbonyl]amino}-3-oxo propyl]disulfanyl}-2-{[(tert-butoxy)carbonyl]amino}propanoate To a suspension of compound obtained in the previous step (5.0 g, 11.3 mmol) in DCM (150 mL) was added dropwise trichloroacetimidate (13.2 mL, 79.4 mmol). The mixture was stirred at room temperature for 2 h, then concentrated under vacuum. The residue was taken-up in DCM (30 mL), the resulting suspension was filtered, and the filtrate was concentrated under reduced pressure. Purification of the residue by column chromatography afforded the title compound (5.10 g, 81%) as a white solid.

MS (ESI$^+$): [M+H]$^+$=553.5

$^1$H NMR (CDCl$_3$, 500 MHz) δ (ppm): 5.31 (bs, 2H); 4.44 (m, 2H); 3.19 (dd, 2H, J=13.7 and 4.5 Hz); 3.11 (dd, 2H, J=13.7 and 5.4 Hz); 1.47 (s, 18H); 1.44 (s, 18H)

Step 3: tert-butyl (2R)-2-{[(tert-butoxy)carbonyl]amino}-3-sulfanylpropanoate

To a solution of previous compound (5.0 g, 9.0 mmol) in THF (50 mL) was added dropwise tributylphosphine (3.35 mL, 13.6 mmol) followed by water (5 mL). The mixture was stirred overnight at room temperature, then concentrated under reduced pressure. Purification of the residue by column chromatography afforded the title compound (2.51 g, 60%) as a white solid.

MS (ESI$^+$): [M+H]$^+$=278.3

Example 1: (2R)-2-amino-3-{[(2S)-2-amino-4-sulfobutyl]disulfanyl}propanoic acid

Step 1: tert-butyl (2R)-3-{[(2S)-2-{[(benzyloxy)carbonyl]amino}-4-[(2,2-dimethylpropoxy) sulfonyl]butyl]disulfanyl}-2-{[(tert-butoxy)carbonyl]amino}propanoate To a solution of benzyl N-[(2S)-1-{[(2S)-2-{[(benzyloxy)carbonyl]amino}-4-[(2,2-dimethylpropoxy)sulfonyl]butyl]disulfanyl}-4-[(2,2-dimethylpropoxy)sulfonyl]butan-2-yl]carbamate (intermediate E described in patent WO2012/045849) (2.0 g, 2.57 mmol) in DMF (35 mL) was added dropwise a solution of tert-butyl (2R)-2-{[(tert-butoxy)carbonyl]amino}-3-sulfanylpropanoate (1.43 g, 5.15 mmol) in DMF (15 mL). After stirring overnight at room temperature, the mixture was evaporated to dryness. The residue was taken-up into EtOH (15 mL) and a solution of iodine in EtOH (380 mg in ca 4 mL) was added dropwise until persistence of a deep orange coloration (~2 mL). The mixture was concentrated under vacuum. Purification of the residue by two consecutive flash chromatographies afforded the title compound (1.20 g, 35%) as a white solid.

MS (ESI$^+$): [M+H]$^+$=665.7

$^1$H NMR (CDCl$_3$, 500 MHz) δ (ppm): 7.37-7.30 (m, 5H); 5.30 (m, 1H); 5.18 (m, 1H); 5.11 (m, 2H); 4.46 (m, 1H); 3.99 (m, 1H); 3.85 (s, 2H); 3.21-3.16 (m, 3H); 3.073.04 (m, 1H); 2.93 (m, 2H); 2.26-2.18 (m, 1H); 2.07-2.04 (m, 1H); 1.46 (s, 9H); 1.44 (s, 9H); 0.97 (s, 9H)

Step 2: (2R)-2-amino-3-{[(2S)-2-amino-4-sulfobutyl]disulfanyl}propanoic acid

To a solution of previous compound (1.1 g, 1.65 mmol) in anisole (400 μL) was added dropwise TFA (2 mL). The mixture was heated at 75° C. upon complete conversion (3 h) and concentrated in vacuo. The residue was dissolved in water and extracted with DCM (six times) and the aqueous layer was concentrated under reduced pressure. Crystallization of the residue in EtOH/H$_2$O (95/5) afforded the title compound (302 mg, 59%) as a white solid.

Estimated purity: 95% (based on NMR)

MS (ESI$^+$): [M+H]$^+$=305.2.

$^1$H NMR (D$_2$O, 500 MHz) δ (ppm): 4.14 (dd, 1H, J=7.5 and 4.2 Hz); 3.90 (quint, 1H, J=6.5 Hz); 3.40 (dd, 1H, J=14.9 and 4.2 Hz); 3.29-3.22 (m, 2H); 3.15-3.11 (m, 2H); 3.08 (dd, 1H, J=14.9 Hz and 7.5 Hz); 2.35-2.23 (m, 2H)

Example 2: (2R)-2-amino-3-{[(3S,4S)-4-amino-1-phenyl-6-sulfohexan-3-yl]disulfanyl}propanoic acid Step 1: (2S)-2-{[(benzyloxy)carbonyl]amino}-4-[(2,2-dimethylpropoxy)sulfonyl]butanoic acid To a solution of ethyl (2S)-2-{[(benzyloxy)carbonyl]amino}-4-[(2,2-dimethylpropoxy) sulfonyl]butanoate (intermediate A described in patent WO2012/045849) (5.9 g, 14.2 mmol, 1.0 eq.) in THF/water (5/1, 60 mL) at room temperature, was added LiOH.H$_2$O (425 mg, 17.8 mmol, 1.25 eq.). The mixture was stirred at room temperature for 2 h. The reaction mixture was diluted with EtOAc and acidified with 1N HCl solution until pH=1. The layers were separated and the aqueous phase was extracted with EtOAc (twice). The combined organic extracts were dried over Na$_2$SO$_4$, filtered and concentrated under reduced pressure to afford the title compound (5.9 g, quantitave yield) as a colorless oil.

MS (ESI$^-$): [M−H]$^-$=386.1; [(M×2)−H]$^-$=773.3

$^1$H NMR (CDCl$_3$, 500 MHz) δ (ppm): 7.43-7.28 (m, 5H); 5.47 (d, J=6.9 Hz, 1H); 5.13 (s, 2H); 4.51 (s, 1H); 3.87 (s, 2H); 3.47-3.05 (m, 2H); 2.51 (s, 1H); 2.27 (s, 1H); 0.98 (s, 9H)

Step 2: benzyl N-[(1S)-3-[(2,2-dimethylpropoxy)sulfonyl]-1-[methoxy(methyl)carbamoyl]propyl]carbamate To a solution of previous compound (5.5 g, 14.2 mmol, 1.0 eq.) in DMF (50 mL) at 0° C., were successively added TBTU (5.01 g, 15.6 mmol, 1.1 eq.) and DIPEA (4.95 mL, 28.4 mmol, 2.0 eq.). The resulting solution was stirred at room temperature for 20 min and then N,O-dimethylhydroxylamine hydrochloride (1.52 g, 15.6 mmol, 1.1 eq.) was added. The mixture was stirred at room temperature for 16 h. The mixture was diluted with MTBE and the organic solution was washed with saturated aqueous solution of NH$_4$Cl. The aqueous phase was extracted with MTBE (3 times) and the combined organic extracts were washed with half-saturated aqueous solution of NaHCO$_3$ (3 times) and brine, dried over Na$_2$SO$_4$, filtered and concentrated under reduced pressure. The residue was purified by column chromatography to afford the title compound (5.15 g, 84%) as a colorless oil.

MS (ESI$^+$): [M+H]$^+$=431.1

$^1$H NMR (CDCl$_3$, 500 MHz) δ (ppm): 7.42-7.28 (m, 5H); 5.63 (d, J=8.5 Hz, 1H); 5.20-5.01 (m, 2H); 4.92-4.67 (m, 1H); 3.85 (s, 2H); 3.78 (s, 3H); 3.29-3.06 (m, 5H); 2.49-2.24 (m, 1H); 2.16-2.05 (m, 1H); 0.97 (s, 9H)

Step 3: benzyl N-[(3S)-1-[(2,2-dimethylpropoxy)sulfonyl]-4-oxo-6-phenylhexan-3-yl]carbamate To a solution of previous compound (5.15 g, 12.0 mmol, 1.0 eq.) in THF (60 mL) at 0° C., was added dropwise a commercially available solution of phenethylmagnesium chloride (1 M solution in THF, 35.9 mL, 35.9 mmol, 3.0 eq.). The resulting mixture was stirred for 3 h before more phenethylmagnesium chloride was added (8 mL, 8 mmol, 0.63 eq.). After stirring a further 1 h at 0° C., the reaction mixture was slowly poured into a saturated aqueous solution of NH₄Cl. EtOAc was added and the layers were separated. The aqueous phase was extracted with EtOAc (twice) and the combined organic extracts were washed with brine, dried over Na₂SO₄, filtered and concentrated under reduced pressure. The residue was purified by column chromatography to afford the title compound (4.75 g, 84%) as a colorless oil.

$^1$H NMR (CDCl₃, 500 MHz) δ (ppm): 7.43-7.02 (m, 10H); 5.53 (d, J=7.5 Hz, 1H); 5.10 (s, 2H); 4.44 (s, 1H); 3.83 (s, 2H); 3.32-2.99 (m, 1H); 2.99-2.67 (m, 5H); 2.43 (td, J=10.2, 5.4 Hz, 1H); 1.99 (m, 1H); 0.96 (s, 9H)

Step 4: benzyl N-[(3S,4R)-1-[(2,2-dimethylpropoxy)sulfonyl]-4-hydroxy-6-phenylhexan-3-yl]carbamate To absolute EtOH (170 mL) at −78° C., was added LiAlH(Ot-Bu)₃ (5.08 g, 20.0 mmol, 2.0 eq.) portionwise, monitoring that the internal temperature did not rise above −50° C. (no full dissolution was observed). After stirring for 40 min at −78° C., a solution of the compound obtained in the previous step (4.75 g, 10.0 mmol, 1.0 eq.) in absolute EtOH (20 mL) was added dropwise over 10 min, monitoring that the internal temperature did not rise above −60° C. The resulting mixture was stirred at −78° C. for 1.5 h, then a 1N HCl (25 mL) solution was added. The resulting mixture was partitioned between EtOAc and water. The layers were separated and the aqueous phase was extracted with EtOAc. The combined organic extracts were dried over Na₂SO₄, filtered and concentrated under reduced pressure. The residue was purified by column chromatography to afford the title compound (4.51 g, 95%) as a colorless oil.

MS (ESI⁺): [M+H]⁺=478.2

$^1$H NMR (CDCl₃, 500 MHz) δ (ppm): 7.53-6.94 (m, 10H); 5.18 (d, J=9.0 Hz, 1H); 5.09 (s, 2H); 3.84 (s, 2H); 3.79-3.54 (m, 2H); 3.29-3.00 (m, 2H); 2.91-2.74 (m, 1H); 2.74-2.54 (m, 1H); 2.21-2.09 (m, 1H); 2.02-1.91 (m, 1H); 1.87-1.71 (m, 2H); 0.96 (s, 9H)

Step 5: benzyl N-[(3S,4R)-1-[(2,2-dimethylpropoxy)sulfonyl]-4-(methanesulfonyloxy)-6-phenylhexan-3-yl]carbamate To a solution of previous compound (2.0 g, 4.19 mmol, 1.0 eq.) in DCM (42 mL) at 0° C., were successively added dropwise methanesulfonyl chloride (389 μL, 5.02 mmol, 1.2 eq.) and DIPEA (1.48 mL, 8.37 mmol, 2.0 eq.). The resulting solution was stirred at room temperature for 2 h. The reaction mixture was partitioned between MTBE and 1N HCl solution. The layers were separated and the aqueous phase was extracted with MTBE. The combined organic extracts were washed successively with 1N HCl solution, brine, then dried over Na₂SO₄, filtered and concentrated under reduced pressure to afford the title compound (2.45 g, quantitative yield) as a white foam.

MS (ESI⁺): [M+H]⁺=556.2

$^1$H NMR (CDCl₃, 500 MHz) δ (ppm): 7.32-7.20 (m, 7H); 7.18-7.07 (m, 3H); 5.31 (d, J=9.7 Hz, 1H); 5.10-4.98 (m, 2H); 4.85-4.76 (m, 1H); 4.04-3.89 (m, 1H); 3.78 (s, 2H); 3.13-2.98 (m, 2H); 2.94 (s, 3H); 2.78-2.58 (m, 2H); 2.17-1.94 (m, 2H); 1.94-1.79 (m, 2H); 0.90 (s, 9H)

Step 6: benzyl N-[(3S,4S)-4-(acetylsulfanyl)-1-[(2,2-dimethylpropoxy)sulfonyl]-6-phenylhexan-3-yl]carbamate To a solution of crude mesylate compound obtained in the previous step (4.19 mmol, 1.0 eq.) in acetone (21 mL) at room temperature, was added AcSK (957 mg, 8.38 mmol, 2.0 eq.). The reaction mixture was stirred at 50° C. for 18 h. The reaction mixture was partitioned between MTBE and saturated aqueous solution of NaHCO₃. The layers were separated and the aqueous phase was extracted with MTBE. The combined organic extracts were washed successively with saturated aqueous solution of NaHCO₃, brine, then dried over Na₂SO₄, filtered and concentrated under reduced pressure. The residue was purified by column to afford the title compound (2.02 g, 90% over two steps) as a light orange oil.

MS (ESI⁺): [M+H]⁺=536.1

$^1$H NMR (CDCl₃, 500 MHz) δ (ppm): 7.42-7.29 (m, 7H); 7.25-7.18 (m, 1H); 7.15 (d, J=7.4 Hz, 2H), 5.20-5.06 (m, 2H); 4.81 (d, J=10.1 Hz, 1H); 4.09 (tt, J=9.6, 4.2 Hz, 1H); 3.86 (s, 2H); 3.68-3.60 (m, 1H); 3.20 (td, J=11.2, 10.4, 5.5 Hz, 1H); 3.10 (ddd, J=14.0, 11.2, 4.5 Hz, 1H); 2.84-2.65 (m, 2H); 2.38 (s, 3H); 2.17-1.78 (m, 4H); 1.00 (s, 9H)

Step 7: benzyl N-[(3S,4S)-1-[(2,2-dimethylpropoxy)sulfonyl]-6-phenyl-4-sulfanylhexan-3-yl]carbamate To a solution of thioacetate compound obtained in the previous step (2.02 g, 3.77 mmol, 1.0 eq.) in degassed MeOH (15 mL, 3 cycles of vacuum—argon purge) at room temperature, was added a solution of LiOH.H₂O (181 mg, 7.54 mmol, 2.0 eq.) in water (1.6 mL). The resulting solution was stirred at room temperature for 1 h. The reaction mixture was partitioned between MTBE and saturated aqueous solution of NH₄Cl. The layers were separated and the aqueous phase was extracted with MTBE. The combined organic extracts were washed with brine, dried over Na₂SO₄, filtered and concentrated under reduced pressure. The residue was purified by column chromatography to afford the title compound (1.72 g, 92%) as a light yellow oil.

MS (ESI⁺): [M+H]⁺=494.1

$^1$H NMR (CDCl₃, 500 MHz) δ (ppm): 7.44-7.29 (m, 7H); 7.26-7.15 (m, 3H); 5.24-5.02 (m, 3H); 4.03 (ddt, J=10.4, 6.2, 3.5 Hz, 1H); 3.88 (s, 2H); 3.29-3.10 (m, 2H); 2.96-2.73 (m, 3H); 2.23-2.08 (m, 1H); 2.03-1.88 (m, 2H); 1.88-1.74 (m, 1H); 1.35-1.24 (m, 1H); 1.00 (s, 9H)

Step 8: tert-butyl (2R)-3-{[(3S,4S)-4-{[(benzyloxy)carbonyl]amino}-6-[(2,2-dimethylpropoxy) sulfonyl]-1-phenylhexan-3-yl]disulfanyl}-2-{[(tert-butoxy)carbonyl]amino}propanoate To a solution of N-chloro benzotriazole (774 mg, 5.04 mmol, 1.5 eq.) and benzotriazole (400 mg, 3.36 mmol, 1.0 eq.) in DCM (25 mL) at −78° C., was added dropwise a solution of thiol compound obtained in the previous step (1.66 g, 3.36 mmol, 1.0 eq.) in DCM (5 mL). The mixture was stirred at −78° C. for 2 h. A solution of tert-butyl (2R)-2-{[(tert-butoxy)carbonyl]amino}-3-sulfanylpropanoate (1.40 g, 5.04 mmol, 1.5 eq.) in DCM (5 mL) was then added dropwise. The reaction mixture was stirred at −78° C. for 4 h. Aqueous solution of Na₂S₂O₃ (1.2 g in 20 mL of water) and saturated aqueous solution of NaHCO₃ (30 mL) were successively added and the mixture was allowed to warm-up to room temperature and stirred at room temperature for 10 min. The layers were separated and the aqueous phase was extracted with DCM (twice). The combined organic extracts were dried over $Na_2SO_4$, filtered and concentrated under reduced pressure to afford an orange oil. The residue was purified by two column chromatography to afford the title compound as a light yellow foam obtained in two fractions of different purity (1.21 g, 47% yield of pure fraction) and (0.91 g, 35% yield of 80% pure fraction).

MS (ESI$^+$): [M+H]$^+$=769.4

$^1$H NMR (CDCl$_3$, 500 MHz) δ (ppm): 7.51-7.04 (m, 10H); 5.08 (s, 2H); 4.52-4.29 (m, 1H); 4.11 (d, J=10.6 Hz, 1H); 3.90 (s, 2H); 3.31-3.12 (m, 3H); 3.05-2.85 (m, 3H); 2.84-2.69 (m, 1H); 2.33-2.22 (m, 1H); 2.12-1.94 (m, 2H); 1.83-1.65 (m, 1H); 1.54-1.43 (m, 18H); 1.00 (s, 9H)

Step 9: (2R)-2-amino-3-{[(3S,4S)-4-amino-1-phenyl-6-sulfohexan-3-yl]disulfanyl}propanoic acid To a solution of disulfide obtained in the previous step (1.2 g, 1.56 mmol, 1.0 eq.) in anisole (4.26 mL, 39.0 mmol, 25 eq.) at room temperature, was added trifluoroacetic acid (6.19 mL, 78 mmol, 50 eq.). The mixture was stirred at reflux for 16 h. After cooling down to room temperature, the reaction mixture was concentrated under reduced pressure. The resulting solid/paste was dissolved in water (120 mL) and the aqueous solution was washed with DCM (4×50 mL). The aqueous phase was lyophilized. The residue was purified by Reverse-Phase Flash Chromatography and the fractions of interest were combined and lyophilized to afford the title compound (500 mg, 78%) obtained as bright white solid in a 93/7 mixture of diastereomers (R,S,S)/(R,R,R).

Estimated purity: >97% (based on LCMS) and 95% (based on NMR)

MS (ESI$^+$): [M+H]$^+$=409.0
MS (ESI$^-$): [M−H]$^-$=407.1

$^1$H NMR (D$_2$O, 500 MHz) δ (ppm): 7.40-7.28 (m, 4H); 7.28-7.22 (m, 1H); 4.04 (dd, J=8.4, 4.0 Hz, 1H); 3.77 (dt, J=7.9, 5.0 Hz, 1H); 3.34 (dd, J=14.8, 4.1 Hz, 1H); 3.10 (dd, J=14.8, 8.4 Hz, 1H); 3.04 (ddd, J=10.6, 5.0, 3.6 Hz, 1H); 3.00-2.88 (m, 3H); 2.82-2.74 (m, 1H); 2.43-2.31 (m, 1H); 2.13-1.98 (m, 2H); 1.94-1.80 (m, 1H)

Example 3: Measurement of APA Activity In Vitro

Measurement of APA activity in vitro is based on the protocol of Goldbarg adjusted to the scale of assaying on microplates (Pro Bind™ 3915) (Chauvel et al., 1994). In vitro, in the presence of calcium ions, APA hydrolyses a synthetic substrate α-L-glutamyl-β-naphthylamide (GluβNa) to glutamate and β-naphthylamine (ONa). A diazotation reaction in acidic medium makes it possible to reveal the β-naphthylamine by formation of a violet-colored complex: spectrophotometric measurement then makes it possible to know the amount of complex formed and, by reference to a standard curve produced with increasing concentrations of β-naphthylamine, to deduce the enzymatic activity of the sample.

Reagents

The Glu-βNa substrate (Bachem) and the β-naphthylamine (Sigma) are dissolved in 50% DMSO (dimethyl sulphoxide) and 0.1 N HCl respectively, and conserved at −20° C. at a concentration of $10^{-2}$ M. The diazotation reaction is carried out in the presence of sodium nitrite (87 mM), ammonium sulfamate (130 mM) and N-(1-naphthyl)-ethylenediamine dihydrochloride (23 mM in 95% ethanol).

Enzymatic Reaction

The reaction takes place at pH 7.4 in 50 mM tris-HCl buffer, in the presence of dithiothreitol (100 eq per eq of inhibitor) and calcium (4 mM CaCl$_2$)); recombinant mouse APA is incubated at 37° C. in the presence of the substrate (200 μM Glu-βNa) and in the presence or absence of various concentrations of the inhibitor to be tested, in a final volume of 100 μL. The reaction is stopped by adding 10 μL of 3N HCl. A standard curve of β-naphthylamine was prepared in parallel by diazotizing increasing concentrations (up to 0.2 mM) of 2-naphthylamine in 0.1 N HCl.

Revelation of the Product Formed

The following are added to each well: 25 μL of sodium nitrite (NaNO$_2$) (mix, wait 5 minutes at room temperature), 50 μL of ammonium sulfamate (mix, wait 5 minutes at room temperature), then add 25 μL of N-(1-naphthyl)-ethylenediamine dihydrochloride (mix, wait for stabilization of the violet color for approximately 30 minutes at 37° C.).

The absorbance is then measured at 540 nm.

The compound EC33 ((S)-3 amino-4-mercapto-butylsulfonic acid) described in application WO 99/36066 was used as a reference compound.

The results reported in Table 1. show that Example 1 and Example 2 exhibit the APA-inhibiting activity.

TABLE 1

In vitro inhibition of aminopeptidase A for exemplified inhibitors

| Examples | Results (μM) |
|---|---|
| 1 | 0.81 ± 0.05 |
| 2 | 0.18 ± 0.02 |

Example 4: Measurement of Brain APA Activity (Ex Vivo Experiments)

Brain APA activity was determined as described above

In vivo, in mice (male, 18-20 g Charles River), Example 1 was administered i.v. (50 mg/kg, in a volume of 200 μL).

In vivo, in DOCA-salt rats (male, 250 g Charles River), Example 2 was administered p.o. (8 mg/kg, in a volume of 400 μL).

For each condition, four to sixteen mice and five to seven rats were used. Animals were sacrificed 180 min after the administration. The brains were immediately removed and homogenized by sonication in 10 vol of ice-cold 50 mM Tris-HCl buffer (pH 7.4). APA enzymatic activity was measured on brain homogenates. For this purpose, aliquots of the tissue homogenate (16 μL) were incubated for 30 min at 37° C. with 200 μM of Glu-βNa, 4 mM CaCl$_2$, and 1 μM bestatin inhibitor, with or without 5 μM EC33, in a total volume of 100 μL of 50 mM Tris-HCl buffer (pH 7.4). Then the assay was pursued as described above.

Figure 1:
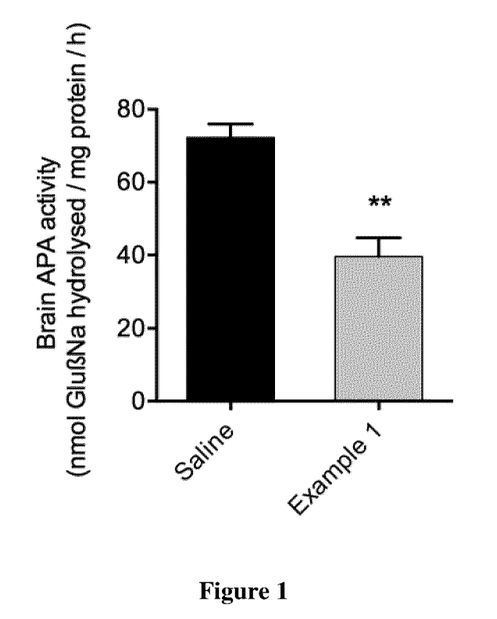
FIG. 1 describes the inhibition of mouse brain APA ex vivo activity after intravenous (i.v.) administration of Example 1 (50 mg/kg).

FIG. 1 demonstrates the ability of Example 1 given by i.v. route to cross the blood brain barrier and to enter the brain by measuring the inhibition of brain APA activity in conscious mice. Example 1 (50 mg/kg, i.v., 3285 nmol per mouse) significantly decreased brain APA activity by 45% after 180 min (39.6±5.2 nmol of Glu-βNa hydrolyzed per mg of protein per h vs. 72.3±3.7, P<0.001, Kruskal-Wallis followed by Dunn's test).

Figure 2:
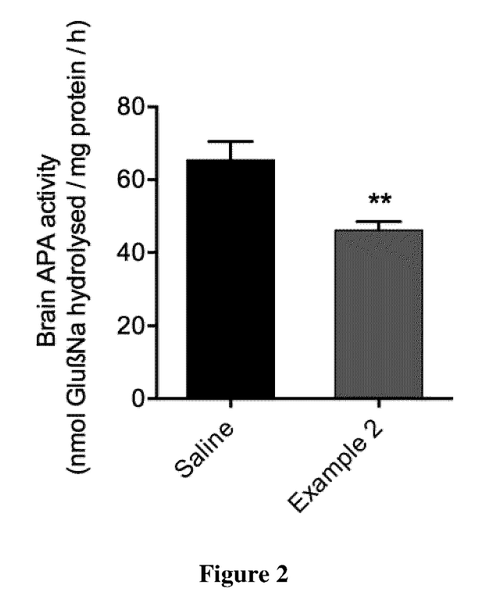
FIG. 2 describes the inhibition of hypertensive rat brain APA ex vivo activity after per os (p.o.) administration of Example 2 (8 mg/kg).

FIG. 2 demonstrates the ability of Example 2 given by p.o. route to cross the blood brain barrier and to enter the brain by measuring the inhibition of brain APA activity in conscious DOCA-salt rat. Example 2 (8 mg/kg, p.o., 4895 nmol per rat) significantly decreased brain APA activity by 29% after 180 min (46.1±2.4 nmol of Glu-βNa hydrolyzed per mg of protein per h vs. 65.4±5.1, P<0.01, Mann-Whitney test).

Example 5: Measurement of Mean Arterial Blood Pressure (MABP) and Heart Rate (HR) (In Vivo Experiments)

Male DOCA-salt rats were anesthetized with 3% isoflurane (Iso-vet®, Piramal, UK) for induction and 1.5-2% isoflurane for maintenance. A catheter was inserted into the right femoral artery to monitor MABP and HR. The catheter was tunneled subcutaneously to exit from the neck. Animals were maintained for 2 days in the animal room, under frequent observation, before MABP and HR recording. Baseline MABP and HR were recorded for at least 60 min before Example 2 was administered p.o. (8 mg/kg, in a volume of 400 µL). MABP and HR were recorded continuously for 6 h after treatment.

Figure 3A:
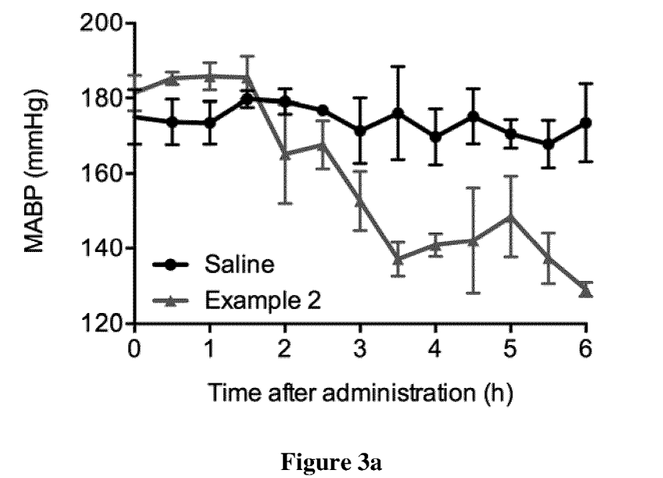
FIG. 3a and 3b demonstrate the effect of p.o. administration of Example 2 (8 mg/kg) on blood pressure and heart rate in hypertensive rats.
Figure 3B:
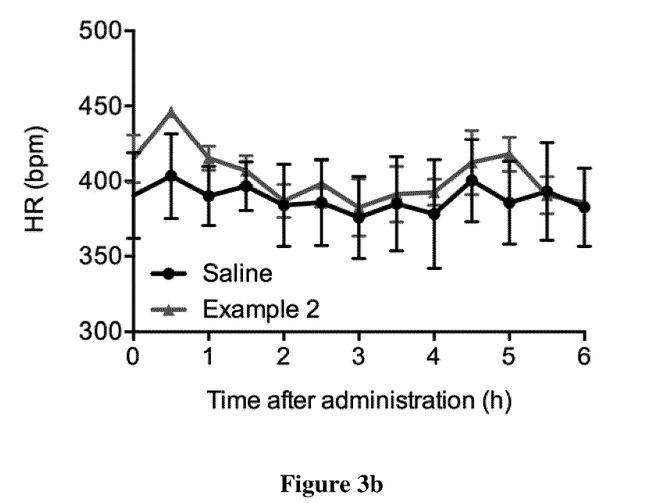

FIGS. 3a and 3b demonstrate the ability of Example 2 given by p.o. route to decrease blood pressure of hypertensive rats by recording MABP and HR in conscious DOCA-salt rats.

In FIG. 3a, Example 2 (8 mg/kg, p.o., 4895 nmol per rat) decreased MABP in hypertensive DOCA-salt rats from 3 h after administration (with a decrease in MABP of −27±11 mmHg), which persisted 6 h after treatment (with a decrease in MABP of −44±8 mmHg).

In FIG. 3b, the p.o. administration of Example 2 (8 mg/kg) had no effect on HR in DOCA-salt rats, regardless of the time elapsed between administration and recording (0 to 6 h).

Example 6: Evaluation of Cardiac Function by Measuring Left Ventricular Ejection Fraction (LVEF) by Echocardiography (In Vivo Experiments)

Experimental Procedures

Adult male CD1 mice were anesthetized with a mixture of 100 mg/kg ketamine (Imalgene 1000, Merial, Lyon, France) and 10 mg/kg xylazine (Rompun 2%, Bayer Healthcare, Loos, France), via intraperitoneal injection, intubated and ventilated at a rate of 200 insufflations/min, with a mean insufflate volume of 0.2 mL (Bioseb, France). The skin was disinfected and incised between the 2nd and 3rd intercostal space and the heart was exposed by left thoracotomy. Pericardium was opened and the left anterior descending (LAD) coronary artery infarction was permanently ligatured between the pulmonary artery trunk and the left atrial appendage, with 8/0 silk suture. (PVDF monofilament, 8-0, Peters Surgical, Bobigny, France). Ischemia was confirmed by visible left ventricle (LV) bleaching under the ligature. The thorax was then closed by three discontinuous points (PVDF monofil, 6/0, Peters Surgical, Bobigny, France) then mice received a subcutaneously injection of Meloxicam 1 mg/kg (Metacam, Boehringer Ingelheim, Germany) for prolonged analgesia. The pneumothorax was drained. The muscles and skin were then sutured (prolene thread 6-0, Peters Surgical, France) and the animals were rehydrated with saline at 37° C. Animals were extubated as soon as they could breathe spontaneously. The animal was placed in a cage and monitored regularly over 48 hours. Mice received an injection of Meloxicam 1 mg/kg, 24 hours postsurgery and up to 72 hours. The same surgical procedure was performed without LAD coronary artery ligation in sham-operated mice.

Post-MI mice received chronic oral treatment firibastat (RB150 used as a reference of brain APA inhibitor) at 150 mg/kg, ramipril (ACE inhibitor as standard treatment) at 1.25 mg/kg, or example 2 at 25 mg/kg with peanut butter vehicle. An adaptation phase was implemented before the start of treatment, in which mice received a dose of peanut butter, applied to the wall of the cage, every morning for one week. Treatment started two days after MI and the different drugs were administered once daily, in the morning, for four consecutive weeks. Cardiac function was evaluated regularly by trans-thoracic echocardiography at 4 weeks post MI to analyze the effects of different chronic oral treatment on heart contractility.

Results

Figure 4:
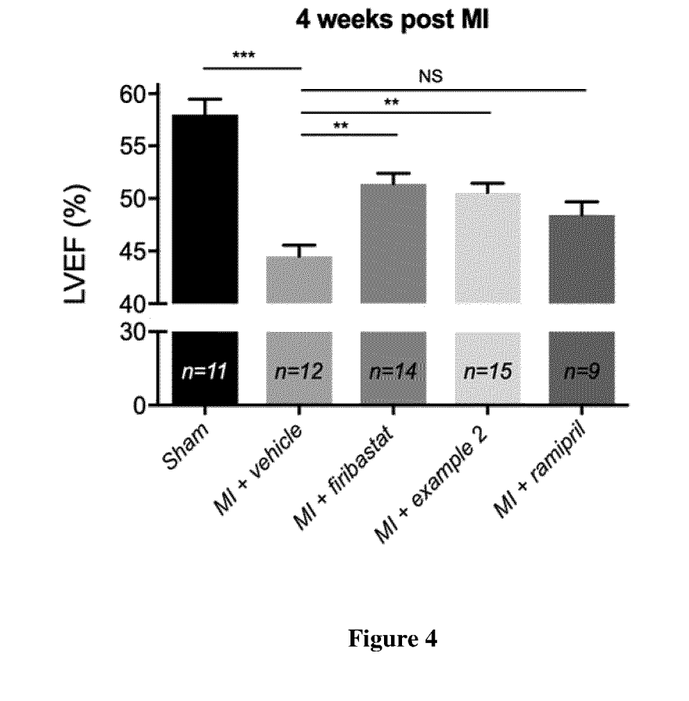
FIG. 4 shows the effects of the chronic oral administration of firibastat, ramipril, or example 2 on left ventricular ejection fraction (LVEF) in mice at 4 weeks post MI. Values are expressed as Mean±SEM from n=9 to n=15.

FIG. 4 shows the effects of the chronic oral administration of firibastat, ramipril, or example 2 on left ventricular ejection fraction (LVEF) in mice at 4 weeks post MI. Values are expressed as Mean±SEM from n=9 to n=15. One-way ANOVA followed by Dunnett's tests. Four weeks post MI, LVEF in vehicle-treated mice was significantly reduced as compared to sham group (FIG. 4) from 58±1.5% n=11 to 44.5±1%, n=12 (p<0.0001) in MI+vehicle mice vs sham-operated mice). The strong decrease of LVEF reflects the deterioration of cardiac contractility post MI. Ramipril and firibastat were included as positive controls in this study. The oral chronic firibastat and ramipril treatments at 1.25 and 150 mg/kg respectively for 4 weeks, improved cardiac function of mice post-MI with a significant LVEF increase in MI+firibastat and MI+ramipril mice as compared to MI+vehicle mice (50.9±1%, n=14 (p=0.0002) in MI+firibastat, 48.4±1.2%, n=9 (p=0.0874) in MI+ramipril mice versus 44.5±1%, n=12 in MI+vehicle mice. In FIG. 4, oral chronic Example 2 treatment (at 25 mg/kg for 4 weeks) significantly increased LVEF of mice post-MI as compared to vehicle treatment, with the same efficacy than firibastat 50.6±0.9%, n=15 (p=0.0007).

CONCLUSION

Example 2 at an oral dose 6 times lower than that used for firibastat, given for 4 weeks, exhibits the same efficiency than firibastat and is even better than the ramipril reference treatment to improve cardiac function in mice post MI.

The invention claimed is:

1. A compound having the following formula (I):

or formula (II):

Wherein:

AH represents —$CO_2H$, —$SO_3H$, —$PO_3H_2$;

m is 1, 2 or 3;

$R_1$ and $R_2$ represent independently H, a $C_{1-6}$ alkyl, $C_{2-6}$ alkenyl or $C_{2-6}$ alkynyl group, each alkyl, alkenyl or alkynyl group being optionally substituted by at least one of the following radicals selected from aryl, heterocycle, cycloalkyl, O-aryl, O-arylalkyl or O-cycloalkyl group; said aryl, heterocycle, cycloalkyl, O-aryl, O-arylalkyl, O-cycloalkyl group being optionally substituted with one or more radicals selected from a halogen atom, an alkyl group, an alkoxy group, a haloalkyl group, a haloalkoxy group, an acyl group, an O-cycloalkyl group, a heteroalkyl group, an O-aryl group, an O-arylalkyl group, an aryl group, a heterocycle group or an arylalkyl group;

a pharmaceutical salt, solvate, zwitterionic form or any prodrug thereof.

2. The compound according to claim 1, wherein $R_1$ and $R_2$ represent independently H or a $C_{1-6}$ alkyl, each alkyl group being optionally substituted by at least one of the following radicals selected from aryl, heterocycle or cycloalkyl group; said aryl, heterocycle, cycloalkyl group being optionally substituted with one or more radicals selected from a halogen atom, an alkyl group, an alkoxy group, a haloalkyl group, a haloalkoxy group, an acyl group, an O-cycloalkyl group, a heteroalkyl group, an O-aryl group, an O-arylalkyl group, an aryl group, a heterocycle group or an arylalkyl group.

3. The compound according to claim 1, wherein $R_1$ and $R_2$ are both H, or, alternatively, $R_1$ is H and $R_2$ is a benzyl or phenethyl group.

4. The compound according to claim 1, wherein the compound corresponds to general formula (I) or formula (II), wherein one, two, three or four of the following features are fulfilled:
   m is 2 or 3; and/or
   AH is $CO_2H$ or $SO_3H$; and/or
   $R_1$ is H; and/or
   $R_2$ is H or an alkyl, preferably an alkyl substituted by a phenyl group.

5. The compound according to claim 1, wherein the compound corresponds to general formula (I) or formula (II), wherein one, two or three of the following features are fulfilled:
   m is 2; and/or
   AH is $SO_3H$; and/or
   $R_1$ and $R_2$ are both H, or, alternatively, $R_1$ is H and $R_2$ is a phenethyl group.

6. The compound according to claim 1, which is selected from the group consisting of:
   (2R)-2-amino-3-{[(2S)-2-amino-4-sulfobutyl]disulfanyl}propanoic acid,
   (2R)-2-amino-3-{[(3S,4S)-4-amino-1-phenyl-6-sulfohexan-3-yl]disulfanyl}propanoic acid, and a pharmaceutical salt, solvate, zwitterionic form or any prodrug thereof.

7. A pharmaceutical composition comprising at least one compound as defined in claim 1 and a pharmaceutically acceptable carrier.

8. The pharmaceutical composition according to claim 7, wherein said compound is selected from the group consisting of:
   (2R)-2-amino-3-{[(2S)-2-amino-4-sulfobutyl]disulfanyl}propanoic acid,
   a pharmaceutical salt, solvate, zwitterionic form or any prodrug thereof.

9. The pharmaceutical composition according to claim 7, wherein said compound has the following formula (I):

or formula (II):

wherein:
   m is 2;
   AH is $SO_3H$; and
   $R_1$ and $R_2$ are both H, or, alternatively, $R_1$ is H and $R_2$ is a phenethyl group.

10. The pharmaceutical composition according to claim 7, wherein said compound has the following formula (I):

or formula (II):

wherein:
   m is 2 or 3;
   AH is $CO_2H$ or $SO_3H$;
   $R_1$ is H; and
   $R_2$ is H, an alkyl, or an alkyl substituted by a phenyl group.

11. The pharmaceutical composition according to claim 7, wherein said compound has the following formula (I):

or formula (II):

wherein:
AH represents —CO$_2$H, —SO$_3$H, —PO$_3$H$_2$;
m is 2 or 3; and
R$_1$ and R$_2$ are both H, or, alternatively, R$_1$ is H and R$_2$ is a benzyl or phenethyl group.

12. A method for prevention or treatment of arterial hypertension and indirectly and directly related diseases, comprising administration to a subject in need thereof of a therapeutically effective amount of a compound according to claim 1.

13. The method according to claim 12, wherein said diseases directly or indirectly related to arterial hypertension are selected in the group consisting of heart disease, heart failure, stroke, peripheral and/or cerebral vascular system diseases, brain, eye and/or kidney diseases.

14. The method according to claim 12, wherein said diseases are selected in the group consisting of primary and/or secondary arterial hypertension, an ictus, myocardial ischemia, cardiac insufficiency, renal insufficiency, myocardial infarction, a peripheral vascular disease, diabetic proteinuria, syndrome X, glaucoma, neurodegenerative diseases and memory disorders.

15. The method according to claim 12, wherein said compound is selected from the group consisting of:
(2R)-2-amino-3-{[(2S)-2-amino-4-sulfobutyl]disulfanyl}propanoic acid,
(2R)-2-amino-3-{[(3S,4S)-4-amino-1-phenyl-6-sulfohexan-3-yl]disulfanyl}propanoic acid, and a pharmaceutical salt, solvate, zwitterionic form or any prodrug thereof.

16. The method according to claim 12, wherein said compound has the following formula (I):

or formula (II):

wherein:
m is 2;
AH is SO$_3$H; and
R$_1$ and R$_2$ are both H, or, alternatively, R$_1$ is H and R$_2$ is a phenethyl group.

17. The method according to claim 12, wherein said compound has the following formula (I):

or formula (II):

wherein:
m is 2 or 3;
AH is CO$_2$H or SO$_3$H;
R$_1$ is H; and
R$_2$ is H, an alkyl, or an alkyl substituted by a phenyl group.

18. The method according to claim 12, wherein said compound has the following formula (I):

or formula (II):

wherein:
AH represents —CO$_2$H, —SO$_3$H, —PO$_3$H$_2$;
m is 1, 2 or 3; and
R$_1$ and R$_2$ are both H, or, alternatively, R$_1$ is H and R$_2$ is a benzyl or phenethyl group.

* * * * *

UNITED STATES PATENT AND TRADEMARK OFFICE
CERTIFICATE OF CORRECTION

PATENT NO. : 11,345,658 B2
APPLICATION NO. : 17/437862
DATED : May 31, 2022
INVENTOR(S) : Fabrice Balavoine et al.

It is certified that error appears in the above-identified patent and that said Letters Patent is hereby corrected as shown below:

In the Specification

Column 2,
Lines 21-22, "(Fournid-Zaluski" should read --(Fournié-Zaluski--.

Column 19,
Line 49, "(ONa)." should read --(βNa).--.

In the Claims

Column 25,
Line 13, "m is 2 or 3; and" should read --m is 1, 2 or 3; and--.

Signed and Sealed this
Fourteenth Day of February, 2023

Katherine Kelly Vidal
*Director of the United States Patent and Trademark Office*